United States Patent
Anvia et al.

(10) Patent No.: US 6,455,003 B1
(45) Date of Patent: Sep. 24, 2002

(54) PRECONCENTRATOR FOR CHEMICAL DETECTION

(75) Inventors: Fredrick Anvia, Costa Mesa; John A. Elton, Irvine, both of CA (US)

(73) Assignee: Femtometrics, Inc., Irvine, CA (US)

( * ) Notice: Subject to any disclaimer, the term of this patent is extended or adjusted under 35 U.S.C. 154(b) by 0 days.

(21) Appl. No.: 09/441,734

(22) Filed: Nov. 17, 1999

(51) Int. Cl.⁷ .................................. G01N 30/96
(52) U.S. Cl. ................. 422/88; 436/178; 422/93
(58) Field of Search .................. 436/178, 119, 436/161, 177; 422/88, 89, 93; 73/23.41, 23.25, 31.07; 250/288; 418/102; 95/87; 96/103

(56) References Cited

U.S. PATENT DOCUMENTS

| | | |
|---|---|---|
| 3,557,532 A | 1/1971 | Broerman |
| 3,675,466 A | 7/1972 | Linenberg |
| 3,768,300 A | 10/1973 | Nemeth |
| 4,584,887 A | 4/1986 | Galen |
| 4,759,210 A | 7/1988 | Wohltjen |
| 4,805,441 A | 2/1989 | Sides et al. |
| 4,895,017 A | 1/1990 | Pyke et al. |
| 4,912,051 A | 3/1990 | Zaromb |
| 4,942,135 A | 7/1990 | Zaromb |
| 5,014,541 A * | 5/1991 | Sides et al. ............... 73/23.41 |
| 5,083,019 A | 1/1992 | Spangler |
| 5,092,157 A | 3/1992 | Achter et al. |
| 5,142,143 A | 8/1992 | Fite et al. |
| 5,162,562 A | 11/1992 | Cohen et al. |
| 5,289,715 A | 3/1994 | Staples et al. |
| 5,395,589 A * | 3/1995 | Nacson ........................ 422/88 |
| 5,469,369 A | 11/1995 | Rose-Pehrsson et al. |
| 5,481,110 A | 1/1996 | Krishnaswamy et al. |
| 5,551,278 A | 9/1996 | Rounbehler et al. |
| 5,695,720 A * | 12/1997 | Wade et al. .................. 422/62 |
| 5,753,832 A | 5/1998 | Bromberg et al. |
| 5,795,368 A | 8/1998 | Wright et al. |
| 5,970,803 A | 10/1999 | Staples et al. |
| 6,223,584 B1 * | 5/2001 | Mustacich et al. ......... 73/23.41 |

FOREIGN PATENT DOCUMENTS

| | | |
|---|---|---|
| GB | 2 250 633 A | 10/1992 |
| WO | WO 97/35174 | 9/1997 |

* cited by examiner

*Primary Examiner*—Jill Warden
*Assistant Examiner*—Sam Siefke
(74) *Attorney, Agent, or Firm*—Knobbe, Martens, Olson & Bear LLP

(57) ABSTRACT

An apparatus for detecting chemicals in a fluid includes a preconcentrator tube connected to a bi-directional pump and to a detector. The preconcentrator tube contains a sorbent material in thermal contact with a heating element. The bi-directional pump pumps fluid in a first direction through the sorbent material, thereby causing some of the chemicals to accumulate on one side of the sorbent material. The bi-directional pump is reversed so as to pump fluid in a second opposite direction, thereby causing the accumulated chemicals to be carried to the detector. The sorbent material is heated while the bi-directional pump is reversed. Preferably, the detector is equipped with a separate pump that draws fluid to the detector.

44 Claims, 7 Drawing Sheets

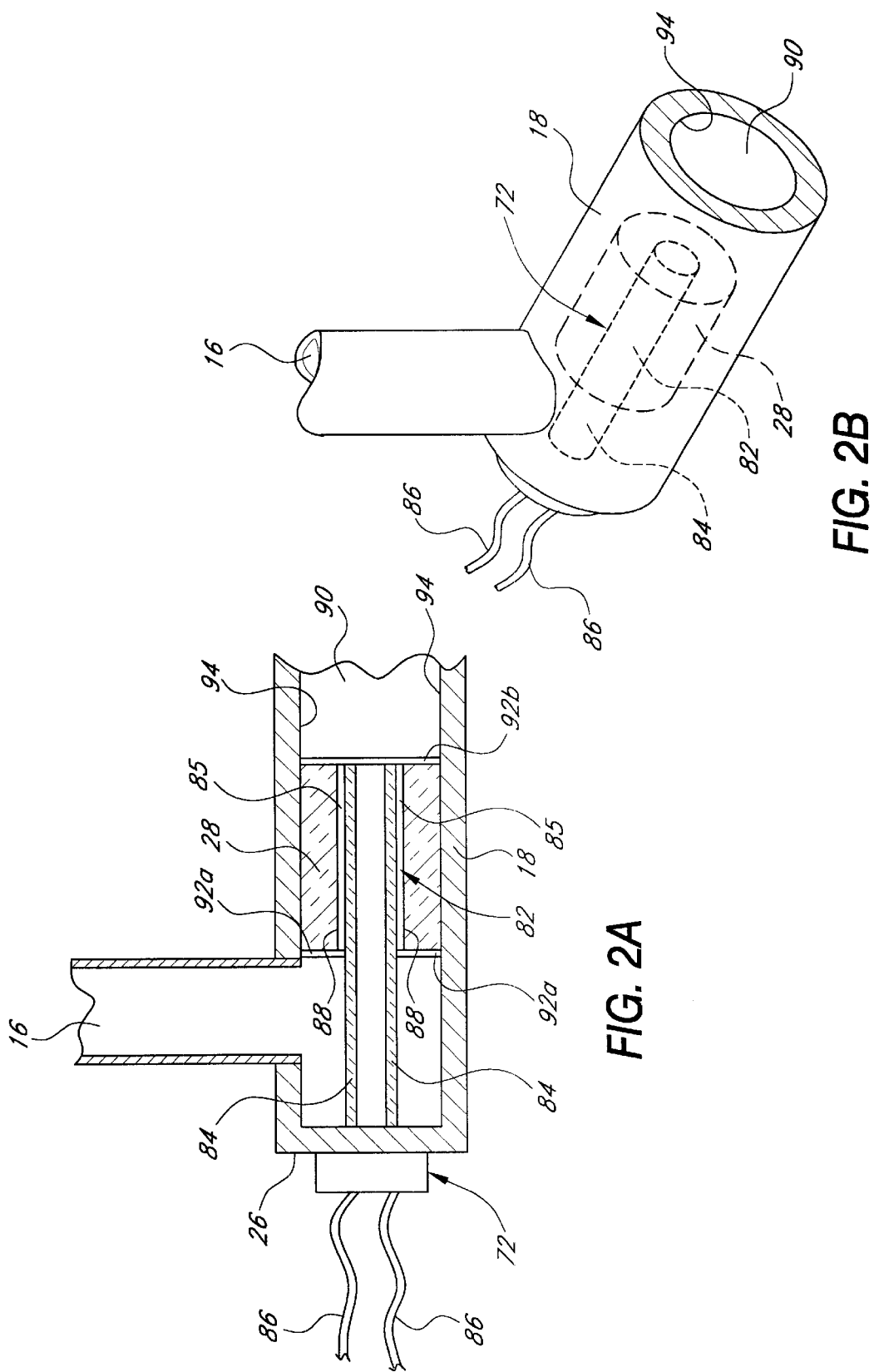

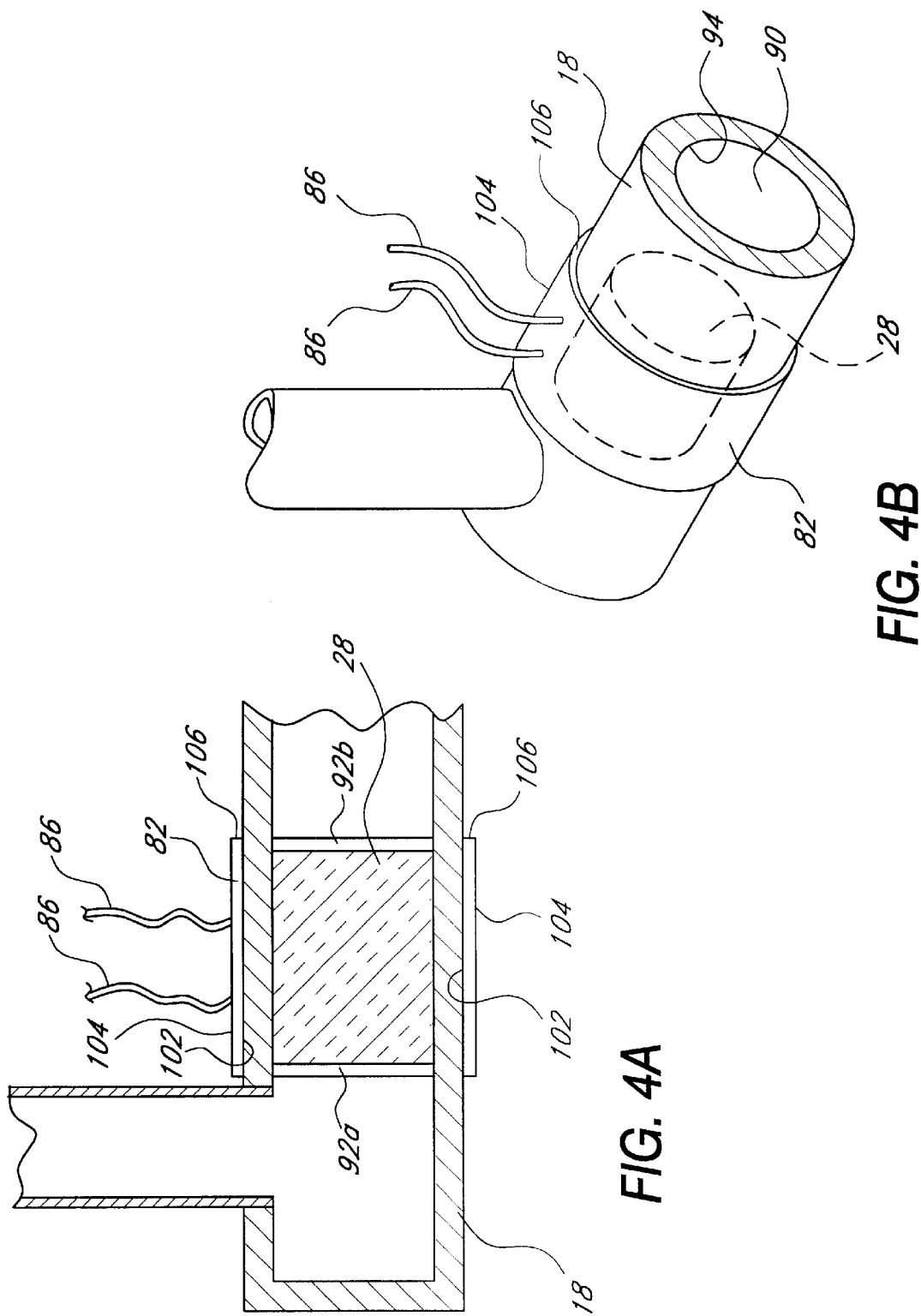

PRECONCENTRATOR FOR CHEMICAL DETECTION

BACKGROUND OF THE INVENTION

The present invention relates to an apparatus for collecting chemical samples, and more specifically, to an apparatus for accumulating a concentration of chemicals over a period of time.

To prevent injury resulting from exposure to toxic chemicals, the presence of toxic chemicals must be detected while their concentrations are below toxic levels. Accordingly, to detect highly toxic chemicals, devices capable of detecting low concentrations within a short period of time are needed.

One prior art device for detecting low concentrations of chemicals includes a pump such as a diaphragm pump and a preconcentrator tube. The pump pumps air through a preconcentrator tube where the chemicals accumulate. The preconcentrator tube may comprise a low thermal mass tube that houses a sorbent material. The terms "preconcentrator tube" and "sorbent material" are well known in the art and correspond to a tube for accumulating chemicals and a material for sorbing (and, therefore, accumulating the chemicals), respectively.

A heating element wrapped around the preconcentrator tube is used to heat the sorbent material and thereby desorb the chemicals. A single pump is used to pump air through the preconcentrator tube and to a detector. Chemicals in the air accumulate in the sorbent material contained within the preconcentrator tube. The heater on the outside of the preconcentrator tube is activated, and chemicals adsorbed onto the sorbent material are released. The chemicals released from the sorbent material are entrained in the air being pumped to the detector.

This prior art configuration is simple and low cost. Additionally, this configuration consumes little power in comparison to other prior art designs. However, one drawback of this prior art configuration is that the detector is unable to measure chemicals contained in the air in real-time since a period of time is required to accumulate chemicals in the sorbent material. During the period of time while the chemicals are accumulating within the preconcentrator tube, the user is blind to the presence of toxic chemicals in the air. This period of time may last several minutes. During this time, the user will be exposed to the chemicals, which may be present in toxic levels. Only when heat is applied to the sorbent material are the chemicals released and detected.

Another disadvantage of this prior art design is that the desorbed chemical must be passed through the entire length of the sorbent material prior to reaching the detector. However, the chemical may react with the sorbent material as it is passed through it. Consequently, a sample of chemical traversing the sorbent material may not accurately reflect the concentration of chemical entering the sorbent material. Additionally, unless the preconcentrator tube is heated for a sufficiently long enough time, all of the chemicals accumulated in the sorbent material will not be released. Again, the sample of chemical released from the sorbent material that reaches the detector may not accurately reflect the concentration of chemical entering the sorbent material. Additionally, the device may exhibit a memory effect in which chemicals remaining in the sorbent material may be released when the preconcentrator tube is heated a subsequent time. Artificially higher levels of chemical may be produced at the detector during this subsequent heating.

Another prior art configuration employs two pumps, a first pump and a second pump, a three-port three-way valve, a preconcentrator tube, and a detector. With the three-port three-way valve in the first position, two separate paths are created. A first path extends from the first inlet to the preconcentrator tube and from the preconcentrator tube to the first pump. A second path extends from the second inlet to the detector and from the detector to the second pump. In a second position, the three-port three-way valve creates a flow path from the second inlet to the preconcentrator tube, from the preconcentrator tube to the detector, and from the detector to the second pump.

With the three-port three-way valve in the first position, air is drawn in the first inlet, pumped through the three-port three-way valve and through the preconcentrator tube, and pumped out an exhaust connected to the first pump. In this manner, chemicals are collected in sorbent material contained inside the preconcentrator tube. Simultaneously, chemicals are drawn from the second inlet through the valve and to the detector. Thus, real-time detection is provided for chemicals present at concentrations high enough to be sensed by the detector.

The first pump is subsequently turned off, the three-port three-way valve is switched to the second position, and a heater surrounding the preconcentrator tube is activated. With the heater activated, the chemicals collected in the sorbent material will be released and drawn into the detector by the second pump.

When the three-port three-way valve is in the second position, the direction that the air is pumped through the preconcentrator tube is reversed. Accordingly, all of the chemicals collected in the sorbent material do not have to travel through the sorbent material to reach the detector, thus, lowering the likelihood of a chemical reaction between the chemicals and the sorbent material. Desorption is also more efficient. The sorbent material does not need to be heated as long since the chemical does not have to pass through all the sorbent material. Despite these advantages, this prior art configuration has serious disadvantages. In particular, the three-port three-way valve is large in volume and requires large amounts of energy such that its use in portable chemical sensor systems is impractical.

A further prior art configuration substitutes the three-port three-way valve employed in the second prior art configuration with three single-port three-way valves that are magnetically latched and consume less power than non-magnetically latched valves. Overall power consumption can be reduced by switching to magnetically latched valves. Although the size of three single-port three-way valves is slightly larger than the size of a single three-port three-way valve, the number of batteries required for the three single-port three-way valves is less. Nevertheless, this configuration requires too much space and energy for many field applications.

Accordingly, there is a need in the art for a chemical detection apparatus that may be miniaturized, is lightweight, and has relatively low power consumption.

SUMMARY OF THE INVENTION

According to one aspect of the invention, an apparatus for detecting one or more chemicals comprises a sorbent element for sorbing the one or more chemicals, a bi-directional pump, and at least one chemical detector. The sorbent element has a fluid flow path therethrough. The bi-directional pump is connected to pump fluid through the fluid flow path of the sorbent element in a first direction during sorption of the one or more chemicals and to pump fluid through the fluid flow path of the sorbent element in a second direction during desorbtion of the one or more chemicals. The at least one chemical detector is connected to receive desorbed chemicals. The apparatus may further comprise an enclosed passageway from the bi-directional pump to the sorbent element and from the sorbent element to the chemical detector. The sorbent element may comprise a tube having a sorbent material therein.

In another aspect of the invention, an apparatus for detecting one or more chemicals comprises a sorbent element having an inlet and an outlet, a bi-directional pump, and a detector comprising a detector housing containing at least one chemical sensor. The sorbent element comprises a sorbent material. The bi-directional pump has an intake and a vent. The bi-directional pump is adapted to pump fluid from the intake to the vent when pumping in a first direction and to pump the fluid from the vent to the intake when pumping in a second direction. The outlet of the sorbent element is connected to the intake of the bi-directional pump such that the fluid flows from the sorbent material to the bi-directional pump when the pump is pumping in the first direction. The inlet of the sorbent element is connected to the detector such that fluid flows from the bi-directional pump to the sensor when the pump is pumping in the second direction. The sorbent element may comprise a porous polymer comprising 2,6 diphenyl-ρ-phenylene oxide. The apparatus may further comprise a detector pump having an intake and a vent, wherein the intake of the detector pump is connected to the detector containing the sensor.

Yet another aspect of the invention comprises a method of detecting one or more chemicals contained in a fluid. This method comprises providing a plurality of flow paths including a first flow path for fluid flow through a sorbent element and a second flow path for fluid flow to at least one chemical detector. The first and second flow paths are connected to respective first and second pumps. The fluid containing the one or more chemicals is inputted into an inlet. A first portion of the fluid containing the one or more chemicals is flowed from the inlet through the first flow path. At least a portion of the one or more chemicals are thereby collected within the sorbent element. A second portion of the fluid containing the one or more chemicals is simultaneously flowed from the inlet through the second flow path to the chemical detector. Fluid is flowed through both of the first and second flow paths without altering the connection of the flow paths with the pumps to deliver the one or more chemicals collected in the sorbent element to the chemical detector. The method may further comprise heating the sorbent element to desorb the one or more chemicals collected in the sorbent element.

BRIEF DESCRIPTION OF THE DRAWINGS

FIG. 2A is a fragmented cross-sectional view of a preconcentrator tube depicting a heating element passing through a sorbent material contained within the preconcentrator tube.

FIG. 2B is a perspective view of the preconcentrator tube and heating element shown in FIG. 2A.

FIG. 4A is a fragmented cross-sectional view of a preconcentrator tube depicting a heating element surrounding the preconcentrator tube.

FIG. 4B is a perspective view of the preconcentrator tube and heating element shown in FIG. 4A.

DETAILED DESCRIPTION OF THE PREFERRED EMBODIMENT

Figure 1:
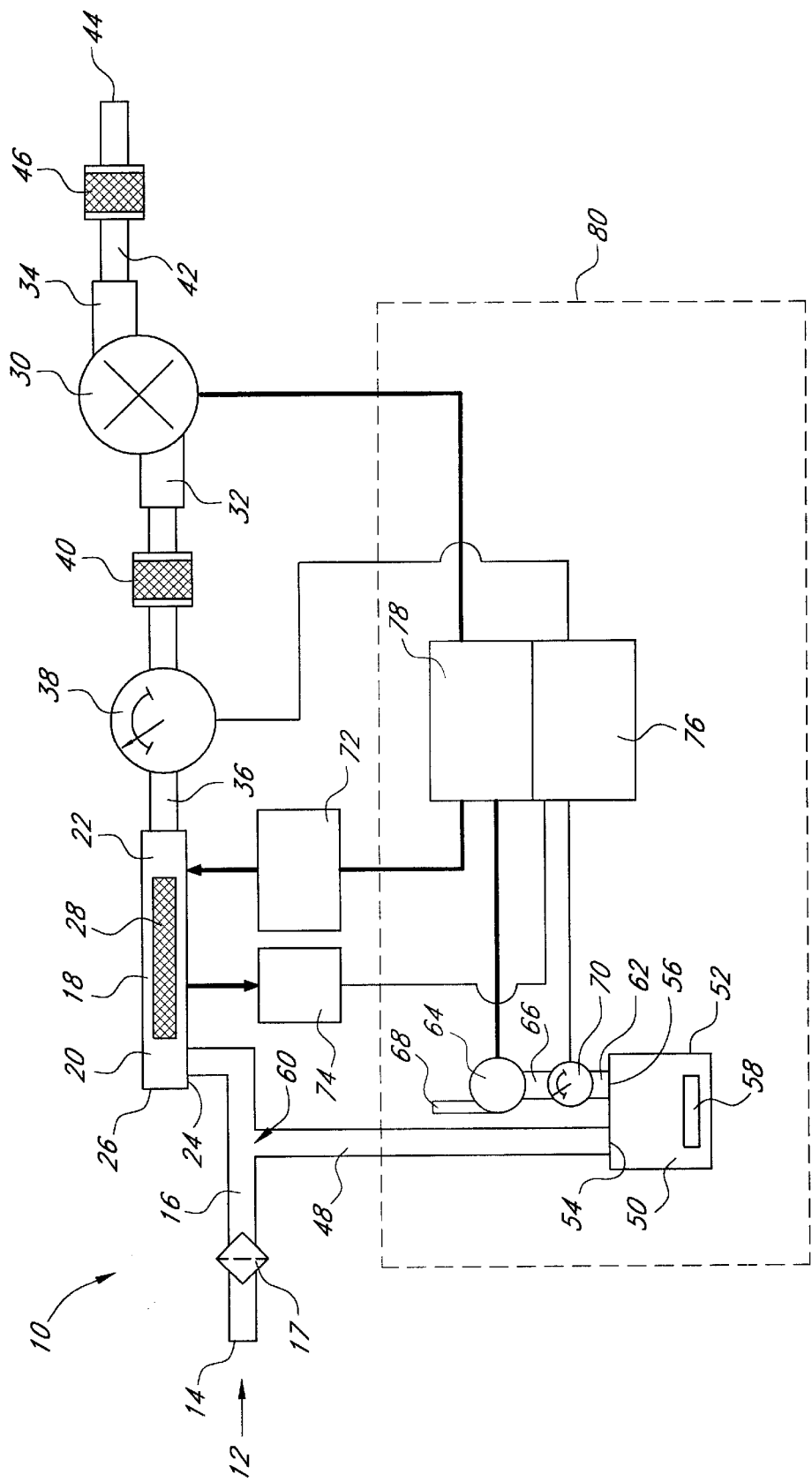
FIG. 1 is a schematic representation of a preferred embodiment of the present invention.

An apparatus 10 for detecting chemicals, such as molecules, in accordance with a preferred embodiment of the present invention is shown in FIG. 1. The apparatus 10 has a primary intake 12, which corresponds to a first opening 14 leading into a primary intake passageway 16. FIG. 1 shows a filter 17 inserted in the primary intake passageway 16, which removes unwanted debris.

The primary intake passageway 16 extends to a preconcentrator element 18 comprising a tube having a front end portion 20 and a rear end portion 22. The primary intake passageway 16 is connected to a side 24 of the preconcentrator tube 18 in the front end portion 20. Although the sorbent (i.e. preconcentrator element) 18 in the embodiment shown in FIG. 1 is in the form of a tube, the present invention is not restricted to the use of a tube as a sorbent element. Chemicals may be accumulated in a chamber having a shape that is not tubular.

As used herein, the term "preconcentrator element," is defined as a structure, such as a tube, for accumulating chemicals. In the preferred embodiment, such accumulation is achieved by a preconcentrator tube 18 containing a sorbent material 28. The sorbent material 28 preferably comprises Tenax® TA 30/60 mesh, which is a porous polymer based on 2,6 diphenyl-ρ-phenylene oxide developed by AKZO Research Laboratories and which can be obtained from Ailtech Associates. Alternatively, the sorbent material 28 may be selected from the group consisting of Tenax® GA, Carbosieve, or granulated charcoal.

Although a tube having sorbent material 28 is employed in the preferred embodiment, any sorbent element 18 may be used to accumulate a concentration of chemicals. For example, the sorbent element 18 may comprise a preconcentrator tube having a coated surface to which the chemicals adhere. Alternatively, the preconcentrator tube 18 may be cooled to promote adsorption on a surface therein. In any case, the sorbent element 18 permits fluid to flow therethrough, while collecting chemicals contained within the flowing fluid.

A bi-directional pump is defined herein as a pump that is capable of pumping fluid in two directions. For example, a bi-directional pump 30 shown in FIG. 1 as having an intake 32 and a vent 34 can pump air from the intake to the vent or from the vent to the intake. Preferably, the bi-directional pump 30 comprises a rotary vane pump. Other types of bi-directional pumps 30 that can be used in accordance with the present invention include blowers and positive displacement pumps. Also, the bi-directional pump 30 preferably is capable of pumping air at a flow rate in the range between 25 and 2000 standard cubic centimeters/minute (sccm).

Most preferably, the bi-directional pump 30 is capable of pumping air at a flow rate in the range between 200 and 1000 sccm.

As shown in FIG. 1, the rearend portion 22 of the preconcentrator tube 18 is connected to an intake 32 on the a bi-directional pump 30 by a passageway 36. A first flow meter 38 and a first scrubber 40 are disposed in the passageway 36 connecting the preconcentrator tube 18 to the bi-directional pump 30. A flow meter measures the flow of air passing through it or other properties related to flow, e.g., rate of flow. A scrubber is defined herein in accordance with its conventional usage to be a filter for purifying a fluid.

Preferably, the first flow meter 38 comprises a bi-directional flow meter, i.e., a flow meter capable of measuring flow passing over a single pathway in either of two directions. In particular, the first flow meter 38 preferably can measure the flow of air from the preconcentrator tube 18 to the bi-directional pump 30 and can measure the flow of air from the pump to the preconcentrator tube.

As shown in FIG. 1, an exhaust line 42 extending from the bi-directional pump 30 has an outlet opening 44, which preferably vents to the ambient atmosphere.

A second scrubber 46 is disposed in the exhaust line 42. Preferably, both the first scrubber 40 and the second scrubber 46 are comprises of the same material as the sorbent material 28 contained within the preconcentrator tube 18. For example, the first scrubber 40 as well as the second scrubber 46 may contain Tenax® TA.

A detector 50 comprises a housing 52 having an entrance orifice 54 and an exit orifice 56. A passageway 48 connects the entrance orifice 54 of the detector housing 52 to a second opening 60 in the primary intake passageway 16. The detector housing 52 preferably contains a sensor array 58 comprising a plurality of sensors capable of sensing the chemicals to be detected. Alternatively, the housing 52 may contain a single sensor.

The sensor array 58 of the preferred embodiment preferably comprises a plurality of surface acoustic wave (SAW) sensors. A chemical sensor array employing an array of SAW devices is disclosed in the application of William D. Bowers, et al. entitled "Chemical Sensor Array", Ser. No. 09/151,747, filed on Sep. 11, 1998, which is hereby incorporated herein by reference. Alternatively, the detector 50 may comprise other chemical detectors including, e.g., a gas chromatograph, an ion mobility spectrometer, or a mass spectrometer.

A separate passageway 62 connects the exit orifice 56 of the housing 52 of the detector 50 to an intake 66 of a detector pump 64 having a vent 68. The detector pump 64 preferably is capable of pumping air at a flow rate in the range between 50 and 500 standard cubic centimeters/minute (sccm) and vents to ambient air. A second flow meter 70 is disposed in the passageway 62 between the detector 50 to the detector pump 64.

Each of the passageways, the primary intake passageway 16, the passageway 36 connecting the preconcentrator tube 18 to the bi-directional pump 30, the exhaust passageway 42 extending from the bi-directional pump, the passageway 48 connecting the primary intake passageway to the detector 50, and the passageway 62 connecting the detector to the detector pump 64 may, in accordance with the present invention, be formed by tubes. Alternatively, the passageways 16, 36, 42, 48, 62, may have shapes other than tubular. For example, the passageways 16, 36, 42, 48, 62, may be formed as integrated flow circuits that are part of a manifold.

FIG. 1 depicts a heater 72 and a temperature sensor 74 in thermal contact with the preconcentrator tube 18 and the sorbent material 28. An electronic controller 76 is electrically connected to a power supply 78, which is electrically connected to the heater 72, the bi-directional pump 30, and the detector pump 64. The first flow meter 38, the second flow meter 70, and temperature sensor 74 are also electrically connected to the controller 76.

As shown in FIG. 1, a detector unit 80 is comprised of the detector 50, the second flow meter 70, the detector pump 64, the electronic controller 76 and the power supply 78. The preconcentrator tube 18, the first flow meter 38, and the bi-directional pump 30 are electrically connected to the detector unit 80. A detector unit 80 and a sample acquisition device for obtaining a gaseous sample from a surface, which may be employed in conjunction with the preferred embodiment of the present invention, is disclosed in the application of William D. Bowers, Ser. No. 09/151,743, filed on Sep. 11, 1998, entitled "Pulsed Air Sampler," which is hereby incorporated by reference.

As best seen in FIGS. 2A and 2B, the heater 72 has a heating element 82 that extends into the preconcentrator tube 18 from the end 26 of the tube. The heating element 82 extends through a central, elongated, longitudinal cavity in the sorbent material 28.

The heating element 82 shown in FIGS. 2A and 2B comprises a film 85 that is formed on the exterior surface of a ceramic tube 84. The film 85 covers at least that portion of the ceramic tube 84 that extends into the longitudinal cavity of the sorbent material 28. The film 85 has a primary surface 88 which is juxtaposed with and in substantial contact with the sorbent material 28. The portion of the ceramic tube 84 not covered with the film 85 is a no heat zone that does not generate heat. Preferably, this film 85 comprises a material, which when deposited, forms a resistive film. More specifically, this film 85 may comprise material selected from the group consisting of indium tin oxide (ITO) films and printed resistive ink films used in the semiconductor industry. This film 85 may also comprise a vapor deposited film, a thick film, or a thin film. The ceramic tube 84 may comprise aluminum oxide. Two heater wires 86, which are connected to the power supply 78, extend from the heater 72. While the resistive film 85 formed on the ceramic tube 84 is shown in FIGS. 2A and 2B, other types of heaters 72 may be employed.

As shown in FIG. 2A, the sorbent material 28 is secured inside 90 the preconcentrator tube 18 with retainer screens 92a, 92b. One of the retainer screens 92a is mounted on the ceramic tube 84 while the other retainer screen 92b is attached to an inside wall 94 of the preconcentrator tube 18. In the preferred embodiment, the sorbent material 28 has a size such that it contacts the inside wall 94 of the preconcentrator tube 18 as shown in FIG. 2A.

Figure 3B:
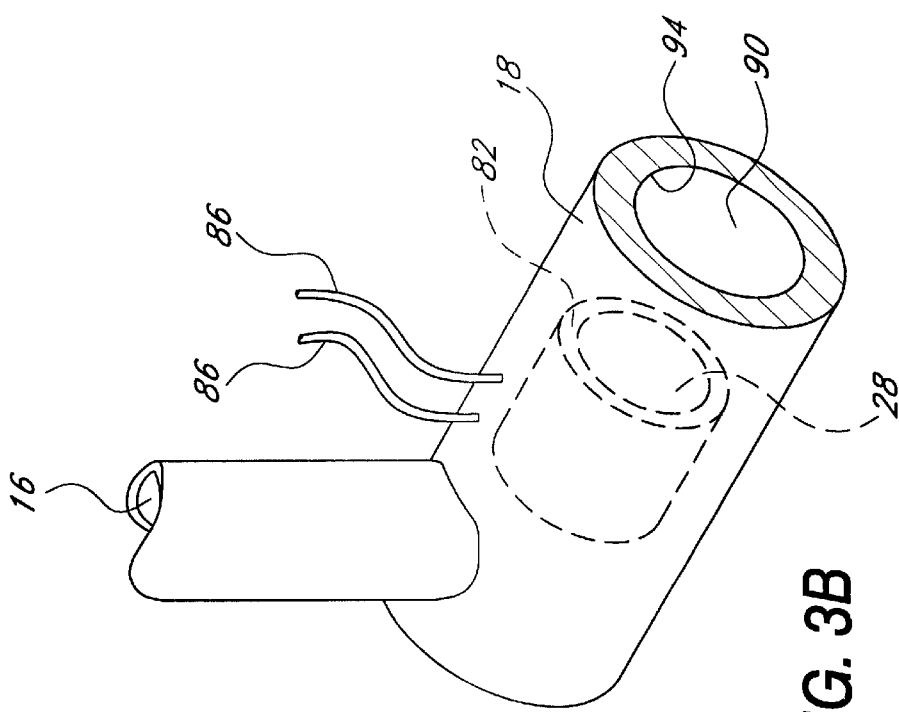
FIG. 3B is a perspective view of the preconcentrator tube and heating element shown in FIG. 3A.
Figure 3A:
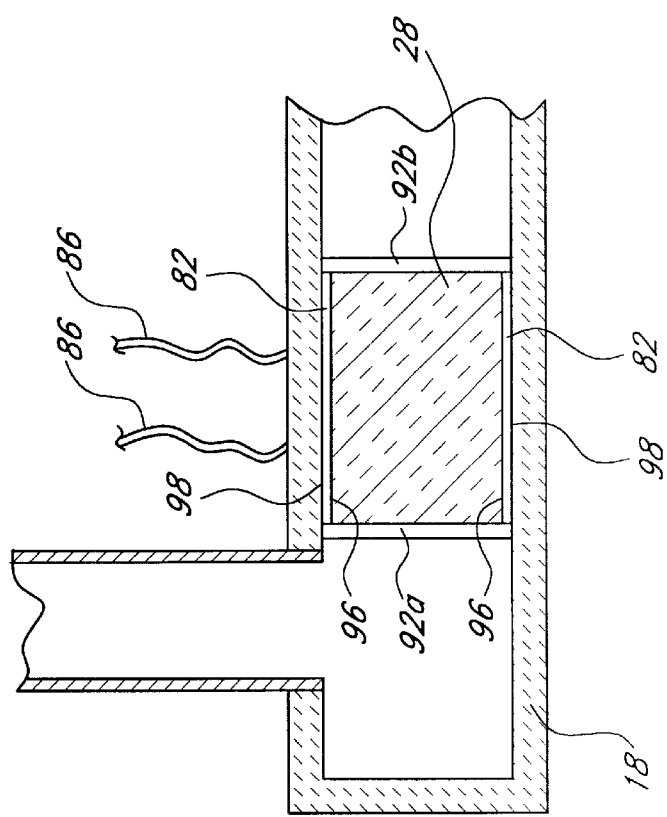
FIG. 3A is a fragmented cross-sectional view of a preconcentrator tube depicting a heating element comprising a heating element interposed between the preconcentrator tube and a sorbent material contained within the preconcentrator tube.

FIGS. 3A and 3B depict the heating element 82 interposed between the preconcentrator tube 18 and the sorbent material 28. This heating element 82 is situated so as to surround the sorbent material 28. The heating element 82 shown in FIGS. 3A and 3B comprises a film formed between the preconcentrator tube 18 and the sorbent material 28. Preferably this film may comprise a material, which when deposited, forms a resistive film. More specifically, this film may comprise material selected from the group consisting of indium tin oxide (ITO) films and printed resistive ink films used in the semiconductor industry. This film may also comprise a vapor deposited film, a thick film, or a thin film.

The heating element 82 shown in FIGS. 3A and 3B has a first surface 96 which is in contact with and is juxtaposed with the sorbent material 28. A second surface 98, opposite to the first surface 96, is juxtaposed with and contacts the inside wall of the tube 18.

The preconcentrator tube 18 depicted in FIGS. 3A and 3B preferably comprises a ceramic. More preferably, the preconcentrator tube 18 comprises a ceramic having low thermal mass (or low mass). Most preferably, the preconcentrator tube 18 also has a low specific heat so as to enable rapid heating and cooling of the preconcentrator tube.

The sorbent material 28 is secured inside 90 the preconcentrator tube 18 with a retainer screens 92a, 92b. In FIG. 3A, each of the retainer screens 92a, 92b is affixed to the inside wall 94 of the preconcentrator tube 18.

FIGS. 4A and 4B depict the preconcentrator tube 18 with the heating element 82 wrapped around it. This heating element 82 is situated so as to surround the preconcentrator tube 18.

The heater 72 shown in FIGS. 4A and 4B comprises a thin foil heater. Two heater wires 86, which are connected to the power supply 78, extend from the heating element 82. Although a thin foil heater is shown in FIGS. 4A and 4B, other heaters 72 that heat the sorbent material 28 from outside the preconcentrator tube 18 may be employed. For example, a current could be passed through a wire wrapped around the preconcentrator tube 18. A wire wound heater comprising heater wire with insulation wound around the wire could be used.

The heating element 82 for the foil heater shown in FIGS. 4A and 4B has a first primary surface 102 which is not in contact with but faces the sorbent material 28.

A second primary surface 104, opposite to the first surface 102, is neither in contact with nor facing the sorbent material 28. The heating element 82 also has end surfaces 106, perpendicular to the first and second primary surfaces 102, 104, which are not in contact nor facing the sorbent material 28.

The preconcentrator tube 18 depicted in FIGS. 4A and 4B preferably comprises a metal, and more preferable low thermal mass metal. Low thermal mass can be achieved with low mass; accordingly, a preconcentrator tube 18 having thin walls may be advantageously employed.

FIG. 4A also shows each of the retainer screens 92a, 92b affixed to the inside wall 94 of the preconcentrator tube 18 and the sorbent material 28 extending to the inside walls of the preconcentrator tube.

As illustrated in FIGS. 2A–2B, 3A–3B, and 4A–4B, the heating element 82 can be either within the sorbent material 28 or outside the sorbent material. However, a heating element 82 within the sorbent material 28 provides more even heating therein. Additionally, heating from within the sorbent material 28 is more efficient and faster. When the heating element 82 is contained within the sorbent material 28, most of the surface area of the heating element will face and be in contact with the sorbent material. Accordingly, less heat is lost by being radiated or conducted away from the sorbent material 28.

For example, the heating element 82 shown in FIGS. 2A–2B is more efficient than the foil heater shown in FIGS. 4A–4B because more of the surface area on the heating element is usable for transferring heat to the sorbent material 28. A substantial portion of the primary surface 88 of the heating element 82 depicted in FIGS. 2A–2B is in contact with or facing the sorbent material 28. Heat, thus, can be transferred to the sorbent material 28 by conduction or radiation through the primary surface 88.

In contrast, although the first primary surface 102 of the foil heater depicted in FIGS. 4A–4B faces the sorbent material 28, the second primary surface 104 does not; and the second primary surface is the same size as the first primary surface. Thus, at least half of the surface area of the foil heater does not participate in the direct transfer of heat to the sorbent material 28. Only the first primary surface 102 of the foil heater directs thermal energy to the sorbent material 28. The end surfaces 106 of the foil heater depicted in FIGS. 2A–2B do not directly transfer heat to the sorbent material 28 since they neither faces nor contact the sorbent material.

Accordingly, the heating element 82 shown in FIGS. 2A–2B is more efficient than the heating element in FIGS. 4A–4B. For example, less heat is radiated away from the sorbent material 28. Additionally, the heating element 82 in FIGS. 2A–2B is directly in contact with the sorbent material 28 while the heater foil shown in FIGS. 4A–4B is not.

The heating element 82 in FIGS. 3A–3B is also more efficient than the heating element in FIGS. 4A–4B. The heating element 82 in FIGS. 3A–3B has a first surface 96 that is in direct contact with and faces the sorbent material 28 whereas the thin foil heater in FIGS. 4A–4B is not in direct contact with the sorbent element.

Figure 5A:
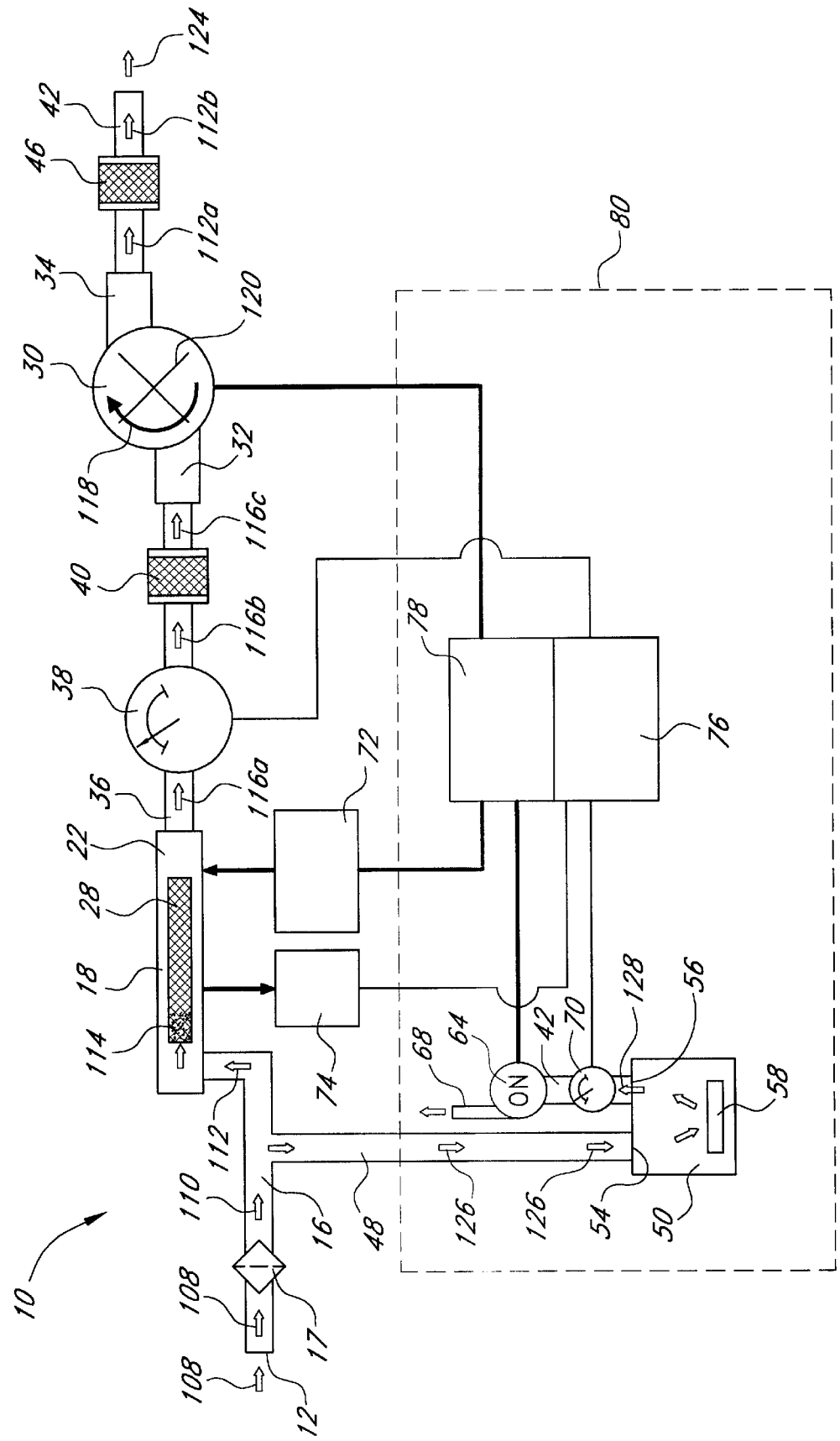
FIG. 5A is a schematic representation of the embodiment shown in FIG. 1 collecting chemicals in the sorbent material.
Figure 5B:
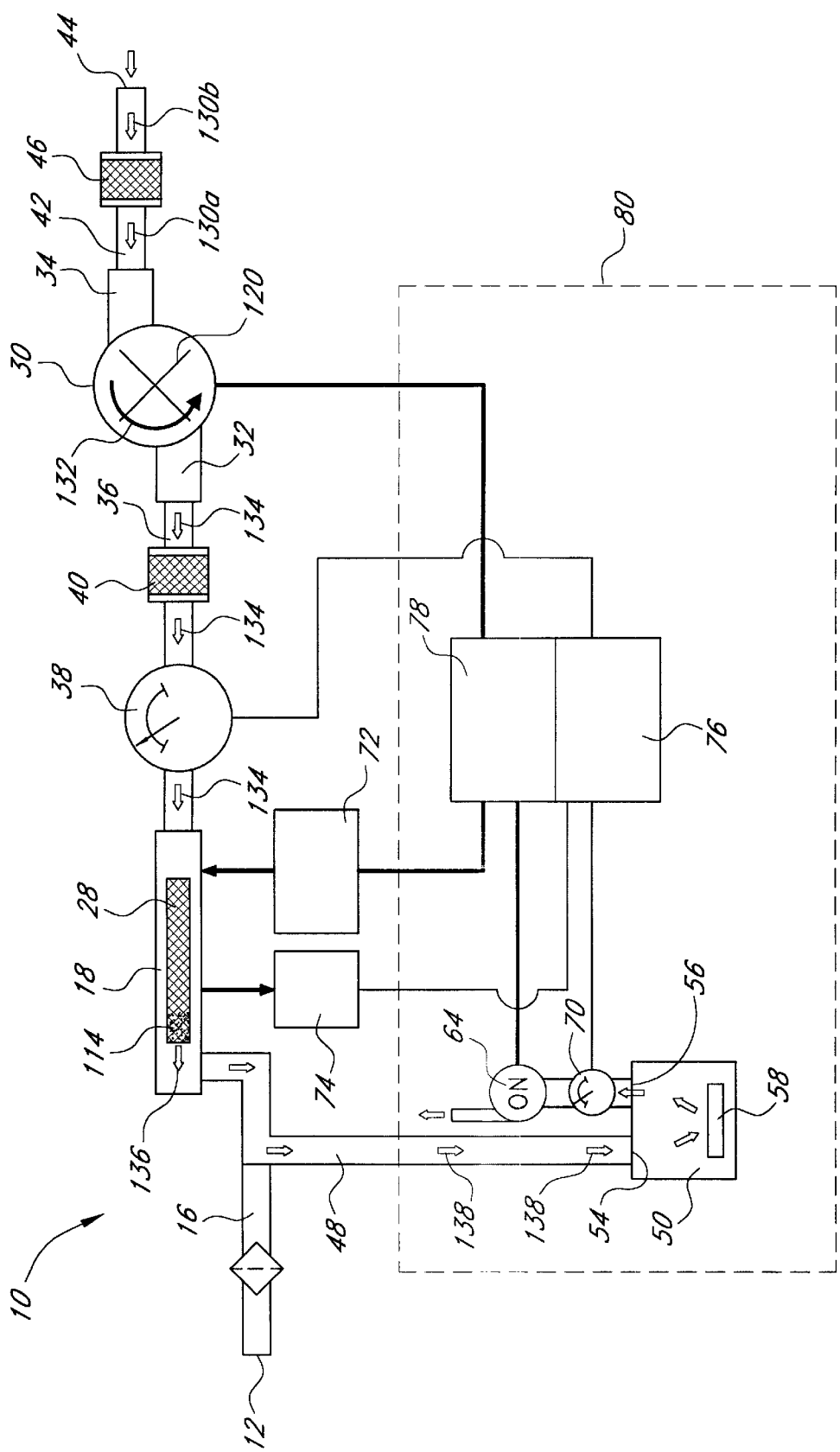
FIG. 5B is a schematic representation of the embodiment shown in FIG. 1 desorbing the chemicals from the sorbent material.

FIG. 5A and 5B depicts the operation of the embodiment shown in FIG. 1. FIG. 5A illustrates a first mode of operation, the collection mode, wherein chemicals are collected in the sorbent material 28. FIG. 5B depicts a second mode of operation, the desorption mode, wherein chemicals collected on the sorbent material are desorbed from it.

In the collection mode, chemicals such as molecules are collected on the sorbent material 28 by activating the bi-directional pump 30 such that air is pulled into the primary intake 12 and through the preconcentrator tube 18. This air is exhausted out the vent 34 of the bi-directional pump 30. To cause the air to flow from the intake 12 through the preconcentrator tube 18, the bi-directional pump 30 operates in a first direction, herein designated as the forward direction.

FIG. 5A shows arrows 108, 110, which represent the flow of air into the primary intake 12 and through the primary intake passageway 16. The air drawn into the primary intake 12 passes through the first filter 17, which removes unwanted debris from the air, thereby preventing this unwanted debris from accumulating on the sorbent material 28.

The air travels from the primary intake passageway 16 into the preconcentrator tube 18 as indicated by another arrow 112. The air entering the preconcentrator tube 18 flows through the sorbent material 28 which traps chemicals 114 therein.

The air exits the rear 22 of the preconcentrator tube 18 and moves into the passageway 36 connecting the preconcentrator tube and the bi-directional pump 30. The air passes through the first flow meter 38 as illustrated by two arrows 116a, 116b. The first flow meter 38 measures the flow or rate of flow through the preconcentrator tube 18 and through the sorbent material 28.

Electrical connection to the controller 76 enables the first flow meter 38 to provide feedback to regulate the rate at which the bi-directional pump 30 passes air through the preconcentrator tube 18. More specifically, the first flow meter 38 outputs a signal indicative of the flow or flow rate through the preconcentrator tube 18 enabling the controller 76 to adjust the pump rate of the bi-directional pump 30 accordingly. The controller 76 will set the power from the power supply 78 that is directed to the bi-directional pump 30, thus, controlling the rate that the bi-directional pumps the air through the sorbent material 28.

The bi-directional pump may also have a tachometer that measures and outputs pump speed (e.g., revolutions/minute). This tachometer can, therefore, provide feedback for controlling the flow rates as well as provide general diagnostics information.

The number density of chemicals 114 collected on the sorbent material 28 is a function of the chemical nature of the sorbent, the concentration of the chemicals in the air, and the total volume of air pumped through the sorbent material. The total volume of air pumped through the sorbent material depends on the flow rate of the air through the sorbent material 28 and the length of time the air passes through the sorbent material. Higher flow rates through the sorbent material 28 mean shorter the times required for collecting a sufficient number density of chemicals for detection. Accordingly, high flow rates through the sorbent material are preferred. These flow rates may range between 25 and 200 standard cubic centimeters/minute (sccm), and more preferably, between 200 and 1000 sccm. Most preferably, the maximum flow rate provided by the bi-directional pump 30 is employed during the collection mode.

Arrows 116b, 116c on two sides of the first scrubber 40 illustrate the passage of the air through a first scrubber prior to entering the bi-directional pump 30. The first scrubber 40 filters out any chemicals that would otherwise reach the bi-directional pump 30. As discussed above, the first scrubber 40 preferably comprises sorbent material that will trap the type of chemicals to be detected at the detector 50. Without the first scrubber 40, these chemicals would reach and contaminate the bi-directional pump 30. As a result, some of these chemicals might be ejected by the bi-directional pump 30 back into the passageway 36 between the preconcentrator tube 18 and the bi-directional pump whenever bi-directional pump pumps in the reverse direction. These chemicals would then flow through the preconcentrator tube 18 and into the detector 50, creating an artificially high reading by the detector. In the preferred embodiment, however, the air in passageway 36 between the preconcentrator tube 18 and the bi-directional pump 30 is pumped through the first scrubber 40 when in the collection mode. Chemicals are trapped in the sorbent material in the first scrubber 40 and do not reach the bi-directional pump 30.

After passing through the first scrubber 40, the air moves into the bi-directional pump 30. The bi-directional pump 30 provides the pumping power to transfer the air from the primary intake 12 and through the preconcentrator tube 18. The bi-directional pump 30 is shown in FIG. 5A as a rotary vane pump. An arrow 118 indicates the motion of the rotor and vanes 120 in the bi-directional pump 30 when the apparatus 10 for detecting chemicals operates in the collection mode.

The air drawn into the bi-directional pump 30 is expelled out the vent 34 of the bi-directional pump and into the exhaust line 42. The air passes through the second scrubber 46 as illustrated by two arrows 122a, 122b on two sides of the second scrubber 46. Another arrow 124 represents the air being discharged from the opening 44 in exhaust line 42.

During the collection mode, while the bi-directional pump 30 pumps air through the preconcentrator tube 18, the detector pump 64 samples air drawn in the primary intake 12 to detect the presence of the chemicals in real-time. In particular, a portion of the air entering the primary intake 12 and passing through the primary intake passageway 16 is drawn by the detector pump 64 into the passageway 48 between the primary intake passageway and the detector 50.

Arrows 126 indicate the flow of air from the primary intake passageway 16, through the passageway 48 between the primary intake passageway and the detector 50 and to the detector. The air enters the detector 50 through the entrance orifice 54 and passes over the sensor array 58. The sensor array 58 detects the presence the chemicals to be detected and outputs a signal, which is communicated to the user of the apparatus IO.

The air passing over the sensor array 58 exits the detector 50 through the exit orifice 56 and enters the passageway 62 between the detector 50 and the detector pump 64 as indicated by another arrow 128. The air proceeds through the second flow meter 70 to the detector pump 64. The air is drawn into the intake 66 of the detector pump 64 and expelled out the vent 68 of the detector pump. The detector pump 64 provides the pumping power to draw a portion of the[]air from the primary intake passageway 16 to the detector 50 while the second flow meter 70 measures the flow or rate of flow through the detector. Electrical connection of the second flow meter 70 to the controller 76 enables the second flow meter to provide feedback to regulate the rate at which the detector pump 64 passes air through the detector 50. More specifically, the second flow meter 70 outputs a signal indicative of the flow or flow rate through the detector 50, thereby enabling the controller 76 to set the power from the power supply 78 that is directed to the detector pump 64.

After a period of time during which chemicals 114 are collected in the preconcentrator tube 18, the apparatus 10 for detecting chemicals is shifted from the collection mode to the desorption mode. In the desorption mode, chemicals 114 collected on the sorbent material 28 are desorbed by activating the heater 72 while air is pumped from the exhaust line 42 of the bi-directional 30 and through the preconcentrator tube 18.

To shift from the collection mode to the desorption mode, the bi-directional pump 30 is switched from pumping in the first direction (i.e. the forward direction) to pumping instead in a second direction, herein designated the reverse direction. Accordingly, the flow of the air through the bi-directional pump 30 and through the pr-econcentrator tube 18 is reversed, as air is pumped from the opening 44 in the exhaust line 42 of the bi-directional pump to the preconcentrator tube.

FIG. 5B depicts the operation of the apparatus for detecting chemicals in the desorption mode. Air is drawn into the opening 44 in the exhaust line 42. This air is pumped through the exhaust line 42 to the bi-directional pump 30. Before reaching the bi-directional pump 30, the air passes through the second scrubber 46 as illustrated by two arrows 130a, 130b.

The second scrubber 46 removes unwanted chemicals from the air entering the exhaust line 42, thereby preventing these unwanted chemicals from entering the bi-directional pump 30. As discussed above, the second scrubber 46 preferably comprises sorbent material that will trap the type of chemicals to be detected at the detector 50. Chemicals are trapped in the sorbent material in the second scrubber 46 and never reach the bi-directional pump 30. Accordingly, these unwanted chemicals will not flow through the preconcentrator tube 18 and into the detector 50, affecting the output of the detector.

The air in the exhaust line 42 proceeds to the bi-directional pump 30 where it drawn into the vent 34 on the bi-directional pump. The bi-directional pump 30 pushes this air out of the intake 32 of the bi-directional pump and into the passageway 36 connecting the bi-directional pump with the preconcentrator tube 18. In this manner, the bi-directional pump 30 provides the pumping power to draw air from the opening 44 in the exhaust line 42 and force the air through the preconcentrator tube 18.

The bi-directional pump 30 is shown in FIG. 5B as a rotary vane pump. An arrow 132 indicates the motion of the rotor and vanes 120 in the bi-directional pump 30 when the apparatus 10 for detecting chemicals operates in the desorption mode. In the case where the bi-directional pump 30 is a rotary vane pump, to switch the direction of the bi-directional pump from the forward direction to the reverse direction, the polarity of the voltage supplied by the power supply 78 to the bi-directional pump is reversed. Switching polarity causes the rotor and vanes 120 to spin in an opposite direction.

Arrows 134 in FIG. 5B represent the flow of air through the passageway 36 connecting the bi-directional pump 30 with the preconcentrator tube 18. FIG. 5B depicts the air passing through the first scrubber 40, which filters out any chemicals released by the bi-directional pump 30. Such chemicals are trapped in the sorbent material in the first scrubber 40 and do not reach the preconcentrator tube 18 or the detector 50.

The air, after passing through the first scrubber 40, continues on through the first flow meter 38, which measures the flow or rate of flow through the preconcentrator tube 18 and through the sorbent material 28. Electrical connection to the controller 76 enables the first flow meter 38 to provide feedback to regulate the rate at which the bi-directional pump 30 passes air through the preconcentrator tube 18.

The air travels from the passageway 36 connecting the bi-directional pump 30 to the preconcentrator tube 18 and on into the preconcentration tube where it flows through the sorbent material 28. The heater 72 is activated when the apparatus 10 is in the desorption mode so as to provide energy to cause the chemicals 114 collected in the sorbent material 28 to be desorbed into the air flowing through the preconcentrator tube 18. These chemicals 114, once desorbed, are carried away by the air flowing through the preconcentrator tube 18 as illustrated by an arrow 136 at the front of the preconcentrator tube shown in FIG. 5B.

Power is supplied to the heater 72 by the power supply 78, which is regulated by feedback from the temperature sensor 74. The temperature sensor 74, in thermal contact with the sorbent material 28 through the preconcentrator tube 18, sends a signal to the controller 76, which then adjusts the amount of power from the power supply 78 that is delivered to the heater 72.

Preferably, the heater 72 heats the sorbent material 18 to a temperature in the range between about 70° C. and 250° C. (200° C. for Tenax®) to desorb chemicals therefrom. More preferably, the temperature controller 76 is programmed to raise the temperature of the sorbent material 28 in stages, holding the temperature at a number of temperature setpoints prior to reaching the temperature at which the chemicals to be detected are desorbed from the sorbent material.

In the case where low concentrations of a chemical are to be detected, a small amount of the chemical may be mixed with a large number of background chemicals. These background chemicals can be present in concentrations that are several orders of magnitude higher than the chemicals of interest. If the preconcentrator tube 18 is heated in a single step to a temperature at which all of the chemicals to be detected are desorbed from the sorbent material, the background chemicals may be released with the chemicals of interest. The release of the background chemicals creates "chemical noise," that is, the detector 50 must be able to distinguish the presence of the chemicals to be detected from the background chemicals.

However, the ability to distinguish the chemicals of interest from other chemicals can be improved by separating the times at which different chemicals are desorbed from the sorbent material 28. The temperature of the sorbent material 28 can be raised in stages, being held for a period of time at one or more temperatures lower than the temperature at which the chemicals to be detected are desorbed from the sorbent material. The high concentrations of background chemicals will then reach the detector at a different time as the chemicals to be detected.

For example, if non-volatile toxic chemicals are to be detected, the preconcentrator tube 18 can be heated first to a temperature lower than the temperature at which the non-volatile toxic chemical is desorbed, then to the temperature at which the non-volatile toxic chemical is desorbed. The background chemicals with low volatility are thereby first driven off the sorbent material 28. Accordingly, chemical noise at the detector 50 is reduced at the point in time when the non-volatile toxic chemical reaches the detector.

The chemicals 114 once desorbed from the sorbent material 28, are carried away by the air flowing through the preconcentrator tube 18 into the primary intake passageway 16. Pumping power to push the air out the preconcentrator tube 18 and into the primary intake passageway 16, is provided by the bi-directional pump 30.

The detector pump 64 continues to draw air into the detector 50 while the apparatus 10 for detecting chemicals is in the desorption mode. Consequently, air being pumped through the preconcentrator tube 18 and into the primary intake passageway 16 is directed into the passageway 48 connecting the primary intake passageway to the detector 50. Arrows 138 indicate the flow of air from the primary intake passageway 16 into the passageway between the primary intake passageway and the detector 50. The air then enters the detector 50 and passes over the sensor array 58. The sensor array 58 detects the presence the chemicals and outputs a signal, which is communicated to the user of the apparatus 10, preferably after some processing.

The detector pump 64 provides the pumping power to draw the air from the primary intake passageway 16 to the detector 50. The second flow meter 70 measures the flow or rate of flow through the detector 50 and provides feedback to the controller 76. The controller 76 is used to regulate the rate at which the detector pump 64 passes air through the detector 50.

Preferably, the bi-directional pump 30 pumps the air through the preconcentrator tube 18 at a rate that is about equal to the rate at which the detector pump 64 pumps air to the detector 50. If the flow rate of air through the preconcentrator tube 18 exceeds the flow rate of air to the detector 50, some air passing through the preconcentrator tube will not enter the passageway 48 connecting the primary intake passageway 16 to the detector 50. Instead, some air will escape through the primary intake 12. Accordingly, some of the chemicals to be detected will not reach the detector 50 for detection. In contrast, if the flow rate of air to the detector 50 exceeds the flow rate of air through the preconcentrator tube 18, additional air drawn in through the primary intake 12 will reach the detector, diluting the concentration of chemicals 114 released from the preconcentrator tube. Thus, the flow rate of air passing through the preconcentrator tube 18, which carries the chemicals 114 out of the sorbent material 28 should be about equal to the flow rate of air to the detector 50. Toward this end, the first and second flow meters 38, 70 can be used to provide feedback to the controller 76, to thereby match the rate of flow of air through the preconcentrator tube 18 with the rate of flow of air to the detector 50. Alternatively, the pressure at the preconcentrator tube 18 could be matched with the pressure at the detector 50. For the foregoing reasons, the measurements made by the detector 50 will be most accurate when the pressure at the preconcentrator tube 18 is approximately equal to the pressure at the detector 50.

Figure 6:
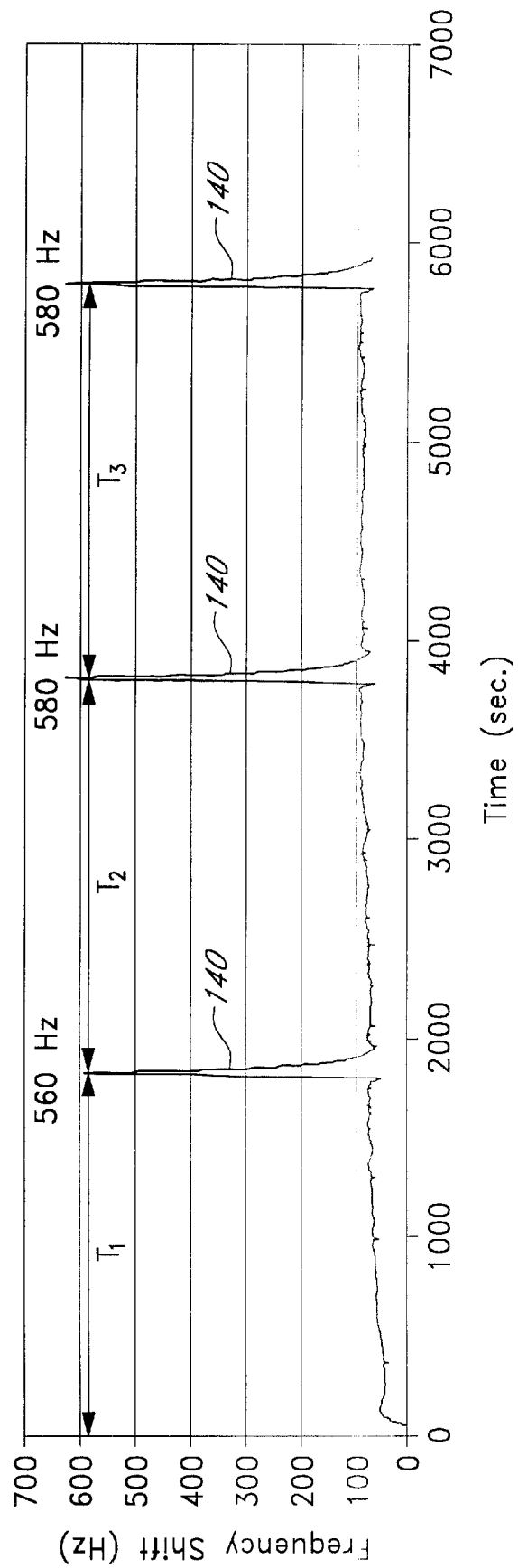
FIG. 6 is a plot, on axes of Time (in seconds) and Frequency Shift (in hertz), which depicts a sensor output during three cycles of collection and desorption.

FIG. 6 illustrates the reproducibility of measurements obtained using the apparatus 10 depicted in FIG. 1 with a SAW sensor as the detector 50. A SAW sensor outputs an oscillating signal having a frequency that shifts when chemicals are adsorbed onto the sensor. This frequency shift, in hertz, is plotted over time, in seconds, to track the output of the SAW sensor during three cycles of collection and desorption. The intervals when the detector pump 64 pumps air across the detector 50 while chemicals collect in the preconcentrator tube 18 correspond to three periods of time $T_1$, $T_2$, $T_3$. The SAW sensor output during these three periods $T_1$, $T_2$, $T_3$ is relatively small, i.e., in the range of between 40 to 100 Hz. In contrast, three peaks 140 results with the release of the chemicals 114 during desorption. The magnitude of the peaks is fairly reproduceable, 560, 580, and 580 Hz, respectively, indicating that chemicals are not randomly released from the preconcentrator tube 18, the first and second scrubbers 40, 46 nor the bi-directional pump 30 during desorption.

Employing a bi-directional pump 30 and reversing its direction to effectuate detection of the chemicals 114 released from the preconcentrator tube 18 eliminates the requirement for a valve to switch the direction of flow through the preconcentrator tube. Without needing such a valve to alter the flow of air, the apparatus 10 for detecting chemicals becomes less complex, smaller in size, and less costly. Additionally, since no valve is required to direct the flow of air during the collection mode and the desorption mode, the apparatus 10 consumes less power.

Switching the direction of pumping of the bi-directional pump 30 reverses the flow through the preconcentrator tube 18, and thus, the thermally desorbed chemicals do not need to proceed completely through the sorbent material 28. The desorbed chemicals only need to travel out the side they were introduced. As a result, the chemicals 114 are less likely to chemically react with the sorbent material 28. Additionally, desorption efficiency is increased, and the sorbent material 28 need not be heated as long. Furthermore, real-time measurement is possible as the detector 50 continuously monitors the air during both the collection and the desorption modes.

Although the preferred embodiment is described as detecting chemicals contained in air, separate embodiments of the invention may be used to detect chemicals in other fluids. Additionally, the apparatus 10 may be employed to detect the presence of chemicals other than molecules, such as sub-micron, neutrally charged chemicals or chemicals in the form of aerosols.

The present invention may be embodied in other specific forms without departing from the essential characteristics as described herein. The embodiments described above are to be considered in all respects as illustrative only and not restrictive in any manner. The scope of any invention is, therefore, indicated by the following claims rather than the foregoing description. Any and all changes which come within the meaning and range of equivalency of the claims are to be considered in their scope.

What is claimed is:

1. An apparatus for detecting one or more chemicals comprising:
   a tube having a sorbent element therein, said element comprising a sorbent material for sorbing said one or more chemicals, said sorbent element having a fluid flow path therethrough for flowing fluid, said sorbent material collecting one or more chemicals contained within the flowing fluid to accumulate at least a portion of said chemicals in said sorbent material;
   a bi-directional pump connected to pump fluid through said fluid flow path of said sorbent element in a first direction during sorption of said one or more chemicals and to pump fluid through said fluid flow path of said sorbent element in a second direction during desorbtion of said one or more chemicals; and
   at least one chemical detector connected to receive desorbed chemicals.

2. An apparatus for detecting one or more chemicals comprising:
   a sorbent element for sorbing said one or more chemicals, said sorbent element having a fluid flow path therethrough;
   a bi-directional pump connected to pump fluid through said fluid flow path of said sorbent element in a first direction during sorption of said one or more chemicals and to pump fluid through said fluid flow path of said sorbent element in a second direction during desorbtion of said one or more chemicals; and
   at least one chemical detector connected to receive desorbed chemicals,
   wherein said bi-directional pump comprises a rotary vane pump.

3. The apparatus of claim 1, further comprising an enclosed passageway from said bi-directional pump to said sorbent element and from said sorbent element to said chemical detector.

4. The apparatus of claim 3, wherein at least a portion of said enclosed passageway comprises an integrated flow circuit contained within a manifold.

5. The apparatus of claim 3, wherein said sorbent element comprises a tube having a sorbent material therein.

6. An apparatus for detecting one or more chemicals comprising:
   a sorbent element for sorbing said one or more chemicals, said sorbent element comprising a tube having a fluid flow path therethrough, said sorbent element having a sorbent material therein;
   a bi-directional pump connected to pump fluid through said fluid flow path of said sorbent element in a first direction during sorption of said one or more chemicals and to pump fluid through said fluid flow path of said sorbent element in a second direction during desorbtion of said one or more chemicals;
   an enclosed passageway from said bi-directional pump to said sorbent element and from said sorbent element to said chemical detector, at least a portion of said enclosed passageway comprising an integrated flow circuit contained within a manifold; and
   at least one chemical detector connected to receive desorbed chemicals,
   wherein said sorbent element comprises a porous polymer comprising 2,6 diphenyl-p-phenylene oxide.

7. An apparatus for detecting one or more chemicals: comprising:
- a sorbent element for sorbing said one or more chemicals, said sorbent element having a fluid flow path therethrough;
- a bi-directional pump connected to pump fluid through said fluid flow path of said sorbent element in a first direction during sorption of said one or more chemicals and to pump fluid through said fluid flow path of said sorbent element in a second direction during desorbtion of said one or more chemicals;
- at least one chemical detector connected to receive desorbed chemicals; and
- a detector pump that pumps said fluid to said chemical detector.

8. The apparatus of claim 7, wherein said detector pump and said bi-directional pump operate simultaneously in said apparatus.

9. An apparatus for detecting one or more chemicals comprising:
- a sorbent element for sorbing said one or more chemicals, said sorbent element having a fluid flow path therethrough;
- a bi-directional pump connected to pump fluid through said fluid flow path of said sorbent element in a first direction during sorption of said one or more chemicals and to pump fluid through said fluid flow path of said sorbent element in a second direction during desorbtion of said one or more chemicals;
- at least one chemical detector connected to receive desorbed chemicals; and
- a heater in thermal contact with said sorbent element.

10. The apparatus of claim 9, wherein said heater comprises a heater element surrounding said sorbent element.

11. The apparatus of claim 10, wherein said heating element comprises a foil heater.

12. An apparatus for detecting one or more chemicals comprising:
- a sorbent element for sorbing said one or more chemicals, said sorbent element having a fluid flow path therethrough;
- a bi-directional pump connected to pump fluid through said fluid flow path of said sorbent element in a first direction during sorption of said one or more chemicals and to pump fluid through said fluid flow path of said sorbent element in a second direction during desorbtion of said one or more chemicals;
- at least one chemical detector connected to receive desorbed chemicals; and
- a first flow meter that measures the flow of said fluid through said sorbent material.

13. The apparatus of claim 12, wherein said first flow meter comprises a bi-directional flow meter.

14. The apparatus of claim 12, further comprising a second flow meter that measures the flow of said fluid to said detector.

15. The apparatus of claim 14, further comprising a controller electrically connected to said first flow meter and to said second flow meter.

16. The apparatus of claim 15, wherein said controller comprises circuitry that causes the rate of flow through said sorbent element to approximate the flow rate through to said detector.

17. The apparatus of claim 9, further comprising a temperature sensor in thermal contact with said sorbent element.

18. The apparatus of claim 17, further comprising heater control circuitry electrically connected to said temperature sensor that controls the temperature of said heater.

19. An apparatus for detecting one or more chemicals comprising:
- a sorbent element for sorbing said one or more chemicals, said sorbent element having a fluid flow path therethrough;
- a bi-directional pump connected to pump fluid through said fluid flow path of said sorbent element in a first direction during sorption of said one or more chemicals and to pump fluid through said fluid flow path of said sorbent element in a second direction during desorbtion of said one or more chemicals;
- at least one chemical detector connected to receive desorbed chemicals;
- an enclosed passageway from said bi-directional pump to said sorbent element and from said sorbent element to said chemical detector; and
- a first scrubber interposed within said passageway at a location between said bi-directional pump and said sorbent element.

20. The apparatus of claim 19, wherein said sorbent element contains sorbent material and said first scrubber comprises the same sorbent material as contained in said sorbent element.

21. An apparatus for detecting one or more chemicals comprising;
- a sorbent element for sorbing said one or more chemicals, said sorbent element having a fluid flow path therethrough;
- a bi-directional pump connected to pump fluid through said fluid flow path of said sorbent element in a first direction during sorption of said one or more chemicals and to pump fluid through said fluid flow path of said sorbent element in a second direction during desorbtion of said one or more chemicals;
- at least one chemical detector connected to receive desorbed chemicals; and
- a second scrubber connected to said bi-directional pump at a position such that when said bi-directional pump pumps said fluid in said first direction, said fluid passes in sequence through said sorbent element, through said bi-directional pump, and through said second scrubber and when said bi-directional pump pumps: said fluid in said second direction, said fluid passes in sequence through said second scrubber, through bi-directional pump, and through said sorbent element.

22. The apparatus of claim 21, wherein said sorbent element contains sorbent material and said second scrubber comprises the same sorbent material as contained in said sorbent element.

23. An apparatus for detecting one or more chemicals comprising:
- a sorbent element for sorbing said one or more chemicals, said sorbent element having a fluid flow path therethrough;
- a bi-directional pump connected to pump fluid through said fluid flow path of said sorbent element in a first direction during sorption of said one or more chemicals and to pump fluid through said fluid flow path of said sorbent element in a second direction during desorbtion of said one or more chemicals; and
- at least one chemical detector connected to receive desorbed chemicals, wherein said fluid flow path is adapted to receive ambient air.

24. An apparatus for detecting one or more chemicals comprising:
  (a) a sorbent element having an inlet and an outlet, said sorbent element comprising a sorbent material;
  (c) a bi-directional pump having an intake and a vent, said bi-directional pump being adapted to pump fluid from said intake to said vent when pumping in a first direction and to pump said fluid from said vent to said intake when pumping in a second direction;
    wherein said outlet of said sorbent element is connected to said intake of said bi-directional pump such that said fluid flows from said sorbent material to said bi-directional pump when said pump is pumping in said first direction; and
  (d) a detector comprising a detector housing containing at least one chemical sensor;
    wherein said inlet of said sorbent element is connected to said detector such that fluid flows from said bi-directional pump to said sensor when said pump is pumping in said second direction.

25. The apparatus of claim 24, wherein said sorbent element comprises a porous polymer comprising 2,6 diphenyl-ρ-phenylene oxide.

26. The apparatus of claim 24, further comprising a detector pump having an intake and a vent, wherein said intake of said detector pump is connected to said detector containing said sensor.

27. The apparatus of claim 24, further comprising a heater in thermal contact with said sorbent material.

28. The apparatus of claim 24, further comprising a first flow meter that measures the flow of said fluid through said sorbent material.

29. The apparatus of claim 28, further comprising a second flow meter that measures the flow of said fluid to said detector.

30. The apparatus of claim 27, further comprising a temperature sensor in thermal contact with said sorbent material.

31. The apparatus of claim 24, further comprising a first scrubber interposed between said sorbent material and said intake of bi-directional pump.

32. The apparatus of claim 31, wherein said first scrubber comprises the same sorbent material as contained in said sorbent element.

33. The apparatus of claim 24, further comprising a second scrubber connected to said vent of said bi-directional pump.

34. The apparatus of claim 33, wherein said second scrubber comprises the same sorbent material as contained in said sorbent element.

35. The apparatus of claim 24, wherein said inlet of said sorbent element is adapted to receive a gas.

36. The apparatus of claim 35, wherein said gas comprises ambient air.

37. A method of detecting one or more chemicals contained in a fluid comprising:
  (a) providing a plurality of flow paths including a first flow path for fluid flow through a sorbent element and a second flow path for fluid flow to at least one chemical detector, said first and second flow paths being connected to respective first and second pumps;
  (b) inputting said fluid containing said one or more chemicals into an inlet;
  (c) flowing a first portion of said fluid containing said one or more chemicals from said inlet through said first flow path, thereby collecting at least a portion of said one or more chemicals within said sorbent element;
  (d) simultaneously flowing a second portion of said fluid containing said one or more chemicals from said inlet through said second flow path to said chemical detector;
  (e) flowing fluid through both of said first and second flow paths without altering the connection of said flow paths with said pumps to deliver said one or more chemicals collected in said sorbent element to said chemical detector.

38. The method of claim 37, wherein said sorbent element comprises a sorbent material.

39. The method of claim 38, wherein said sorbent material comprises a porous polymer comprising 2,6 diphenyl-ρ-phenylene oxide.

40. The method of claim 37, wherein said flow paths are uninterrupted by valves.

41. The method of claim 40, wherein substantially no fluid is expelled from or drawn into said inlet while said one or more chemicals collected in said sorbent element are delivered to said chemical detector.

42. The method of claim 37, further comprising heating said sorbent element to desorb said one or more chemicals collected in said sorbent element.

43. The method of claim 37, wherein (e) further comprises reversing fluid flow through said first flow path without reversing the fluid flow through the second flow path.

44. The method of claim 37, wherein (b) comprises inputting ambient air.

* * * * *